(12) United States Patent
Finger et al.

(10) Patent No.: US 11,020,000 B2
(45) Date of Patent: *Jun. 1, 2021

(54) LUMINESCENT OPHTHALMIC DEVICE

(71) Applicant: IP LIBERTY VISION CORPORATION

(72) Inventors: Paul T. Finger, New York, NY (US); Toby Welles, New York, NY (US)

(73) Assignee: IP LIBERTY VISION CORPORATION, New York, NY (US)

(*) Notice: Subject to any disclaimer, the term of this patent is extended or adjusted under 35 U.S.C. 154(b) by 69 days.

This patent is subject to a terminal disclaimer.

(21) Appl. No.: 16/182,352

(22) Filed: Nov. 6, 2018

(65) Prior Publication Data

US 2019/0239743 A1 Aug. 8, 2019

Related U.S. Application Data

(63) Continuation of application No. 14/243,623, filed on Apr. 2, 2014, now Pat. No. 10,117,578.

(51) Int. Cl.
*A61F 9/00* (2006.01)
*A61B 3/14* (2006.01)
*A61B 3/00* (2006.01)

(52) U.S. Cl.
CPC .............. *A61B 3/14* (2013.01); *A61B 3/0008* (2013.01); *A61F 9/0008* (2013.01); *A61F 9/0017* (2013.01)

(58) Field of Classification Search
CPC ..... A61B 3/0008; A61F 9/0026; A61F 9/0008
See application file for complete search history.

(56) References Cited

U.S. PATENT DOCUMENTS 7,070,554 B2 * 7/2006 White .................. A61N 5/1017 600/3
10,117,578 B2 * 11/2018 Finger .................. A61F 9/0017

* cited by examiner

*Primary Examiner* — Laura A Bouchelle
(74) *Attorney, Agent, or Firm* — Smith Tempel; Steven P. Wigmore

(57) ABSTRACT

A luminescent ophthalmic device for administering therapeutic materials, the device having at least one luminescent marker disposed in proximity to a therapeutic agent applicator so as facilitate placement in a treatment position when viewed using transcorneal or transpupillary viewing methods.

20 Claims, 5 Drawing Sheets

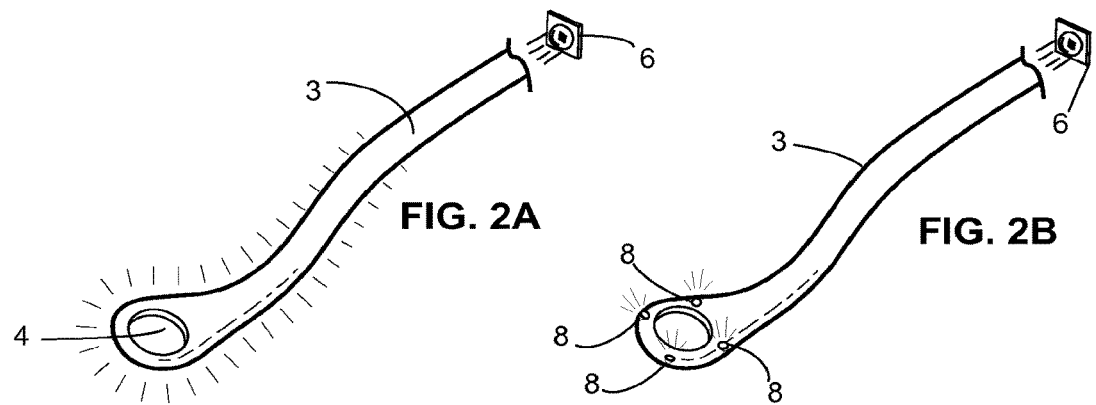
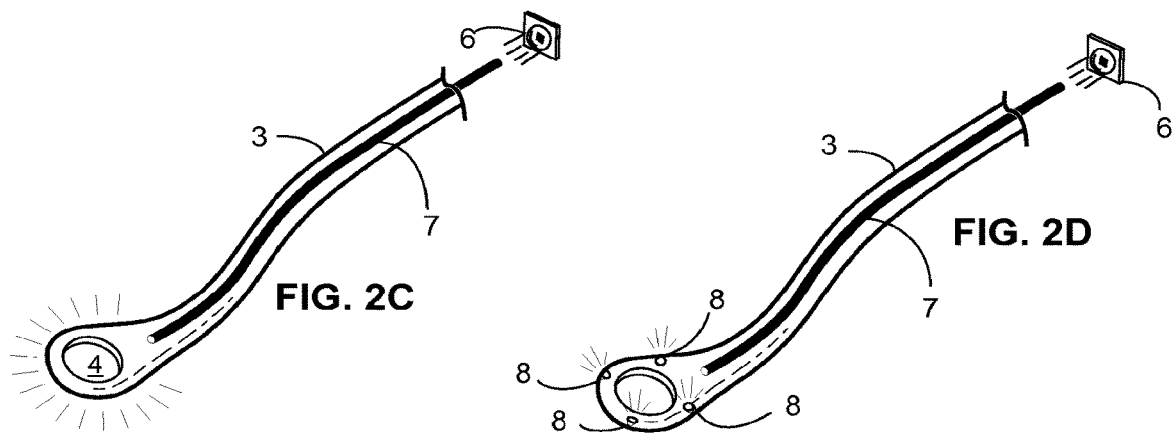
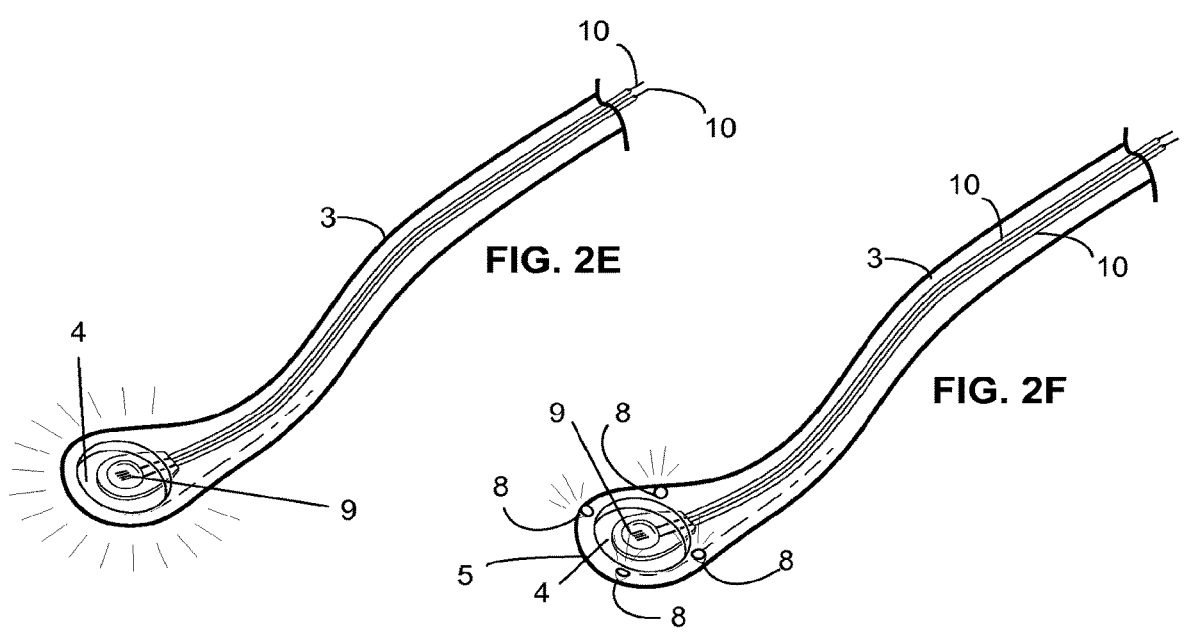

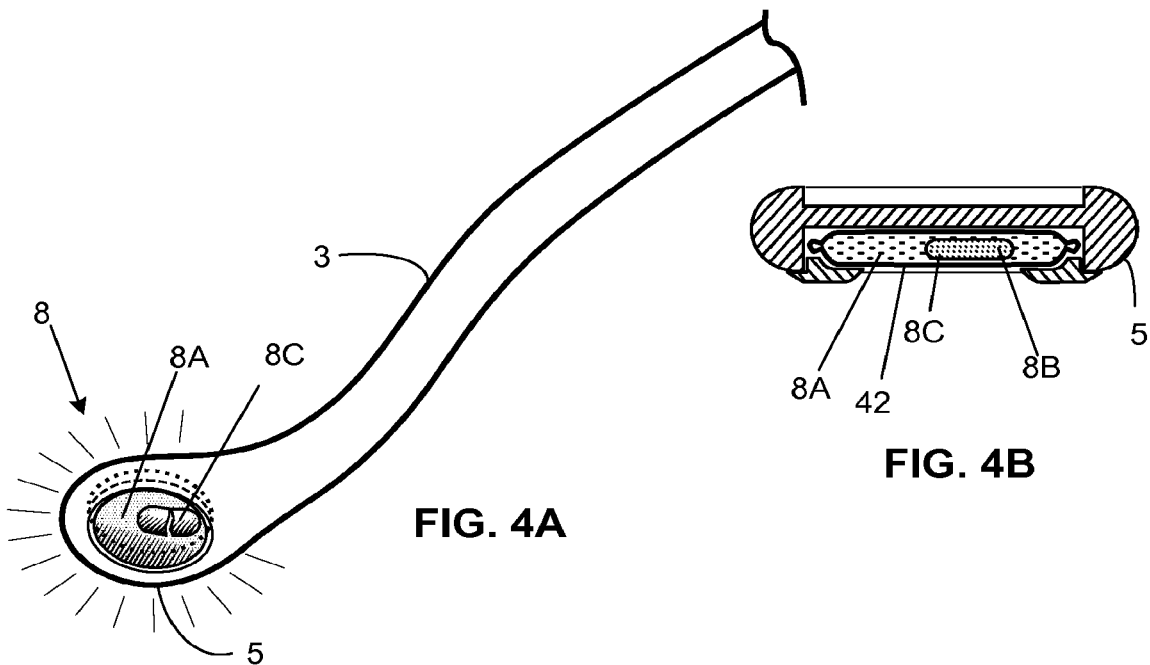
FIG. 4A
FIG. 4B
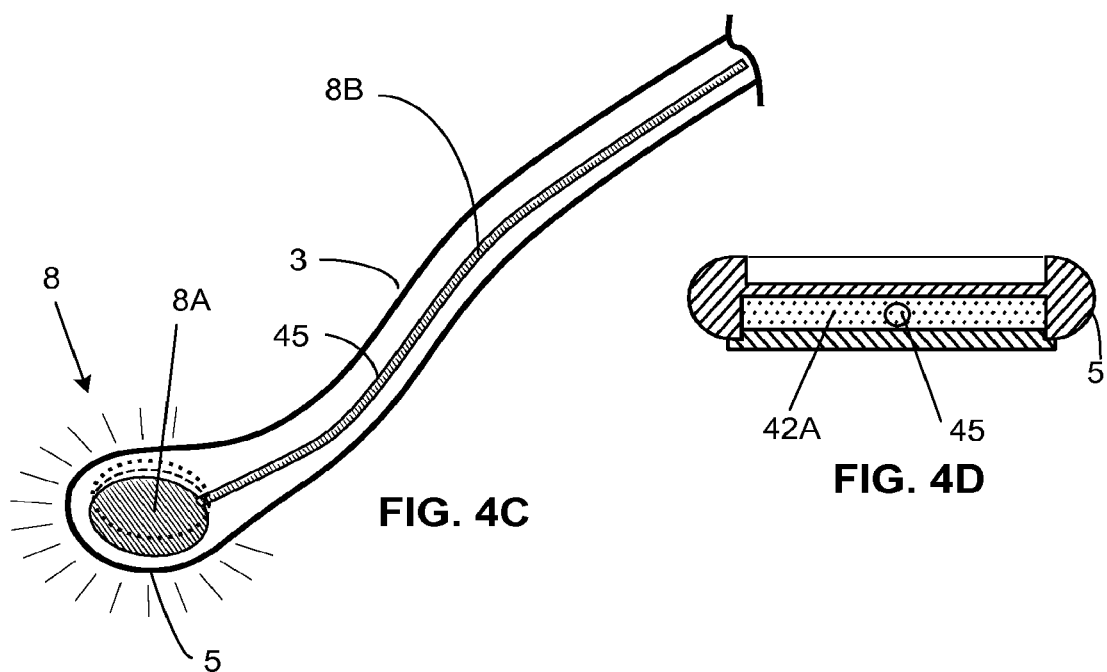
FIG. 4C
FIG. 4D

LUMINESCENT OPHTHALMIC DEVICE

CROSS REFERENCE TO RELATED APPLICATIONS

This application claims the benefit of U.S. Ser. No. 61/922,463, filed on Dec. 31, 2013, which is incorporated by reference herein in its entirety.

BACKGROUND OF THE INVENTION

The present invention relates to the placement of therapeutic substances on or near the posterior portion of an eye globe, and specifically, relates to luminescent reference markers visible through transpupillary viewing methods to facilitate placement of therapeutic substances in the treatment area.

BRIEF DESCRIPTION OF THE DRAWINGS

The subject matter regarded as the invention is particularly pointed out and distinctly claimed in the concluding portion of the specification. The features, their interaction, method of operation, and advantages may be understood with reference to the following detailed description in view of the accompanying drawings in which:

FIG. 2A is a schematic view of a phosphorescent wand of the luminescent ophthalmic device depicted in FIG. 1 depicting a wand body energized from light propagating through the wand body, according to an embodiment;

FIG. 2B is a schematic view of the wand of the luminescent ophthalmic device depicted in FIG. 1 depicting phosphorescent markers energized by light propagating through the wand body, according to an embodiment;

FIG. 2C is a schematic view of the wand of the luminescent ophthalmic device depicted in FIG. 1 depicting a phosphorescent tip driven by light propagating through a light pipe embedded in the wand body, according to an embodiment;

FIG. 2D is a schematic view of the wand of the luminescent ophthalmic device depicted in FIG. 1 depicting phosphorescent markers driven by light propagating through a light pipe embedded in the wand body, according to an embodiment;

FIG. 2E is a schematic view of the wand of the luminescent ophthalmic device depicted in FIG. 1 depicting a phosphorescent tip driven by a light emitting diode arrangement embedded in the wand tip, according to an embodiment;

FIG. 2F is a schematic view of the wand of the luminescent ophthalmic device depicted in FIG. 1 depicting phosphorescent markers driven by a light emitting diode arrangement embedded in the wand tip, according to an embodiment;

FIG. 4A is a schematic view of the wand of the luminescent ophthalmic-device of FIG. 1 depicting a wand tip having a luminescent marker implemented as an in-situ mixing pouch for chemiluminescent chemicals, according to an embodiment;

FIG. 4B is a schematic, cross-sectional view of the in-situ embodiment of the chemiluminescent marker of FIG. 4A, according to an embodiment;

FIG. 4C is a schematic view of the wand of the luminescent ophthalmic-device of FIG. 1 depicting the wand tip includes a luminescent marker implemented as an integral chemiluminescent chamber fed from a feed line disposed in the wand, according to an embodiment;

FIG. 4D is a schematic, cross-sectional view of the fed chemiluminescent chamber embodiment of the chemiluminescent marker of FIG. 4C, according to an embodiment;

It will be appreciated that for clarity of illustration, device elements may be depicted in a manner not to scale and reference numerals may be repeated among the figures to indicate corresponding elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. Well-known methods, procedures, and components have not been described in detail so as not to obscure the present invention.

The present invention related to the treatment of ophthalmic conditions and specifically, relates to the use of luminescent materials to facilitate placement of a therapeutic agent on or in a defined treatment area.

The following terms will used throughout the following document.

The term "luminescence" refers to emission of light through non-incandescent processes. For the purpose of this document, luminescent emission does not refer to light emissions used as markers emanating directly from light emitting diodes.

The term "fluorescence" refers to the emission of electromagnetic radiation responsively to the absorption of incident radiation, the emission persisting only as long as the incident radiation is applied.

The term "phosphorescence" refers to the emission of electromagnetic radiation responsively to the absorption of incident radiation persisting after removal of the incident radiation.

The term "chemiluminescence" refers to the emission of electromagnetic radiation responsively to a chemical reaction.

"Wand" or "wand body" refers to an elongated ergonomic structure extending from a handle and supporting a therapeutic-agent holder at its distal end. The wand is contoured to provide optimal access, visibility, and control, and fatigue-preventative ergonomics for the practitioner.

"Illumination marker", "light marker", and "marker" all refer to the luminescent reference points facilitating proper placement of a therapeutic material in conjunction with transcorneal or transpupillary viewing methods.

Figure 1:
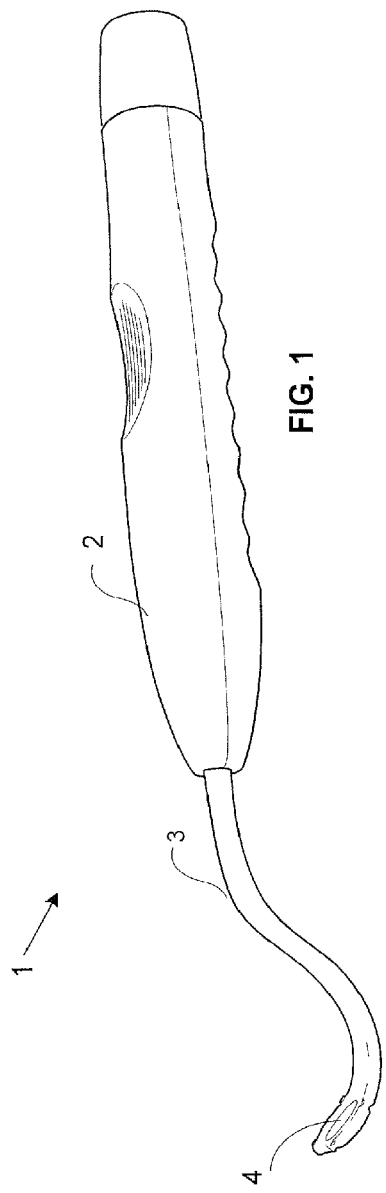
FIG. 1 is a schematic, perspective view of an ophthalmic device having luminescent markers facilitating placement of a therapeutic source in a treatment area, according to an embodiment.

Turning now to the figures, FIG. 1 depicts an ophthalmic, ophthalmic treatment device 1 configured to facilitate application of a therapeutic agent to the posterior portion of an eye globe when viewed using transpupillary viewing methods like, inter alia, transpupillary ophthalmoscopy, optical coherence tomography and videography.

Ophthalmic treatment device 1 includes handle 2 and wand 3 having a cavity 4 for receipt of therapeutic agent.

In a certain embodiment, the distal end of wand 3 exhibits an indentation facilitating abutment with anatomical features having a similar surface profile.

FIGS. 2A-2F depict various phosphorescent-based embodiments in which phosphorescent materials serving as visual markers are activated by ultra-violet (UV) or other wavelengths. Without limiting in scope, this document will discuss UV light as the activation wavelength.

An example of a suitable material providing the luminescence is fluorescein; however, it should be appreciated that materials exhibiting such functionality are included within the scope of the present invention.

In construction of a certain embodiment the luminescent material is embedded in the wand body 3 when extruded, molded or assembled.

In operation, an activation light is applied to luminescent markers 5 causing them to emit light visible that may be used as a reference by a practitioner using transpupillary viewing methods to reliably place the therapeutic agent in a proper treatment area, as noted above. It should be appreciated that the use of luminescent markers for the placement of either radioactive or non-radioactive, therapeutic materials is also within the scope of the present invention.

It should be appreciated that non-integral light pipes attached to the wand and also light sources disposed in proximity to the markers are both included within the scope of the present invention.

Specifically, FIG. 2A depicts a light transmissive, phosphorescent wand 3 configured to fluoresce responsively to propagating through wand 3 from a UV light source 6, according to an embodiment. As noted above, the florescence facilitates proper placement of a therapeutic agent disposed in cavity 4.

FIG. 2B depicts an embodiment in which markers 8 fluoresce responsively to light propagating through wand 3 from UV light source 6. In this embodiment wand 3 is implemented from a light transmissive material like, inter alia, polycarbonate polysulfone, and glass, for example.

FIG. 2C depicts an embodiment in which the wand tip 5 fluoresces responsively to propagating through light pipe 7 from ultra-violet UV light source 6, according to an embodiment.

FIG. 2D depicts an embodiment in which markers 8 fluoresce responsively to UV light propagating through light pipe 7 from UV source 6.

FIG. 2E depicts an embodiment in which the wand tip 5 fluoresces responsively to UV light emitted from UV emitting diodes 9 disposed in wand tip 5, according to an embodiment.

FIG. 2F depicts an embodiment in which markers 8 fluoresce responsively to UV light emitted from UV emitting diodes 9 disposed in wand tip 5, according to an embodiment. It should be appreciated that non-LED sources of UV light are also included within the scope of the present invention.

Figure 3A:
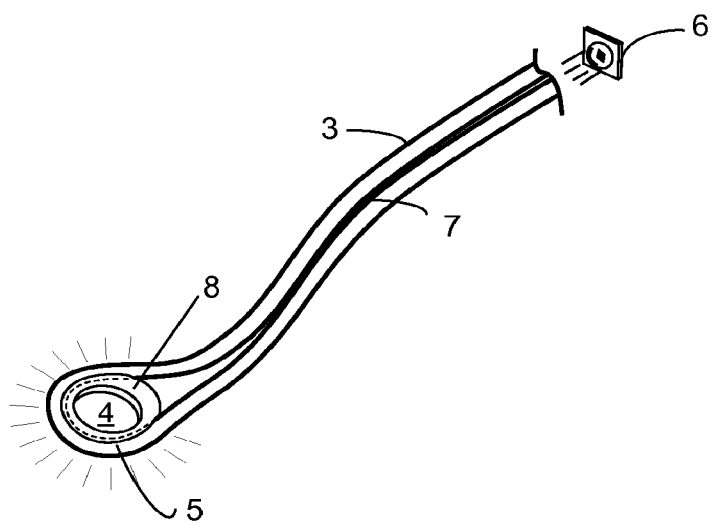
FIG. 3A is a schematic view of the wand of the luminescent ophthalmic device depicted in FIG. 1 depicting a light-activated, photoluminescent marker surrounding a cavity for holding a therapeutic agent, the marker energized by light having propagated through a light guide implemented as the wand body, according to an embodiment.
Figure 3B:
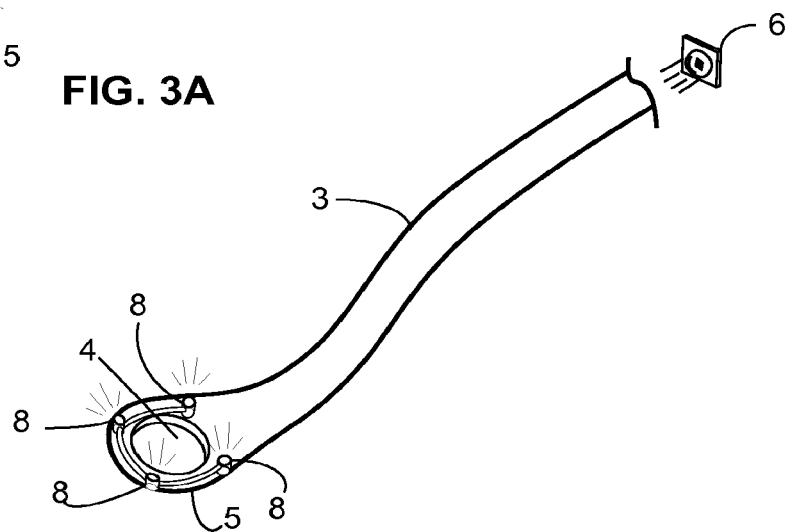
FIG. 3B is a schematic view of the wand of the luminescent ophthalmic device depicted in FIG. 1 depicting a wand tip having photoluminescent markers molded into an otherwise light transmissive, non-photoluminescent wand body and energized by light having propagated through a light guide implemented as the wand body, according to an embodiment.
Figure 3C:
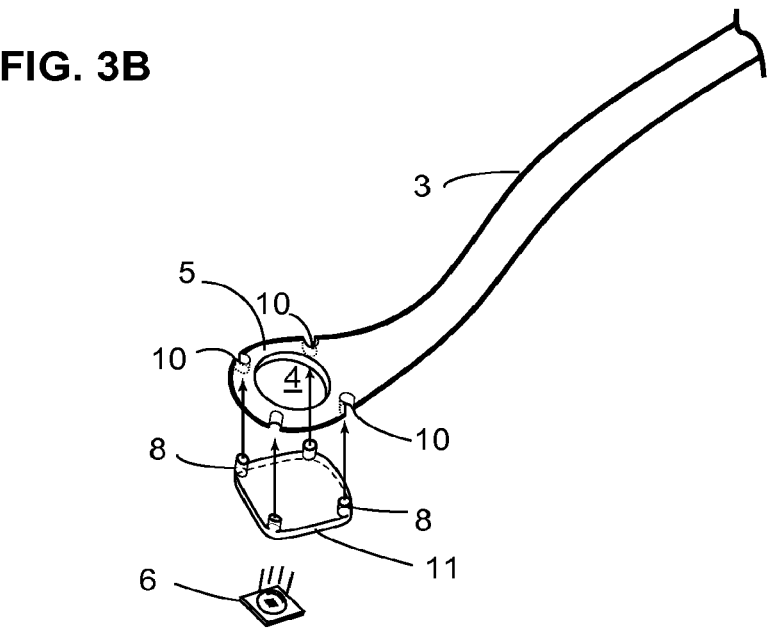
FIG. 3C is a schematic view of the wand of the luminescent ophthalmic device depicted in FIG. 1 depicting a connectable photoluminescent marker unit, according to an embodiment.

FIGS. 3A-3C depict photoluminescent embodiments of wand 3 in which photoluminescent materials are activated or which are energized prior to placement in a treatment area. In a certain a certain embodiment, a secondary light source may boost the photoluminescent materials after the original charge.

Activations sources include, inter alia, various types of particle radiation like beta particles or other charged particles or various electromagnetic radiation like radio waves, microwave, infrared, visible light, x-ray, or gamma ray.

Suitable photoluminescent materials include, inter alia, alkaline-earth aluminate, silicic acid salt, and luminescent pigments. It should be appreciated that other materials exhibiting photoluminescence are also included within the scope of the present invention.

Specifically, FIG. 3A depicts wand 3 formed having embedded light pipes 7 through which activation light emanating from light source 6 energizes a wrap-around rod of photoluminescent material 8 surrounding cavity 4 disposed in tip 5, according to an embodiment.

FIG. 3B depicts light transmissive wand 3 through which activation light emanating from light source 6 energizes photoluminescent markers 8 disposed in tip 5, according to an embodiment.

FIG. 3C depicts light transmissive wand 3 through which activation light emanating from light source 6 energizes photoluminescent markers 8 formed from photoluminescent pegs of an attachment tip 11, according to an embodiment. Tip attachment tip 11 forms a floor of cavity 4 in which a therapeutic agent (not shown) is disposed. Corresponding peg openings 10 are configured to receive pegs 8 defining a line circumscribing the therapeutic agent when attached, according to an embodiment. It should be appreciated that various connection configurations are included within the scope of the present invention; such examples include, inter alit, threading arrangements and flex tabs.

FIGS. 4A-4C depict various chemiluminescent embodiments of wand 3 in which photoluminescent markers 8 are activated through a chemical reaction of chemiluminescent reactants. Examples of suitable reactants include highly oxidized molecules, such as peroxide, and luminol, $C_8H_7N_3O_2$, or diphenyl oxalate, $C_{14}H_{10}O_4$. It should be appreciated that other reactants exhibiting such chemiluminescent functionality are also included within the scope of the present invention.

Specifically, FIGS. 4A and 4B depict wand 3 having a chemiluminescent marker 8 implemented as a flexible mixing pouch 42 disposed underneath light-transparent distal end 5 of wand 3, according to an embodiment.

As shown, a first chemiluminescent reactant 8A is held within pouch 42 and a second chemiluminescent reactant 8B is held separately in a sealed via 8C, according to an embodiment.

In operation, vial 8C is breached upon application of pressure thereby releasing second chemiluminescent reactant 8B into mixing pouch 42 with first chemiluminescent reactant 8A where the reactants 8A and 8B mix and release luminescence of marker 8.

FIGS. 4C and 4D depict a first variant embodiment of a chemiluminescent marker 8 implemented as an integral chemiluminescent reservoir or chamber 42A disposed in wand tip 5 containing first chemiluminescent reactant 8A. Second chemiluminescent reactant 8B is fed through a feed line 45 disposed in wand 3, into the distal chamber 8A where reactants 8A and 8B mix and provide the needed luminescence. It should be appreciated that in a certain embodiment a premixed chemiluminescent mixture is fed through feed line 45 into chamber.

Figures 4E, 4F:
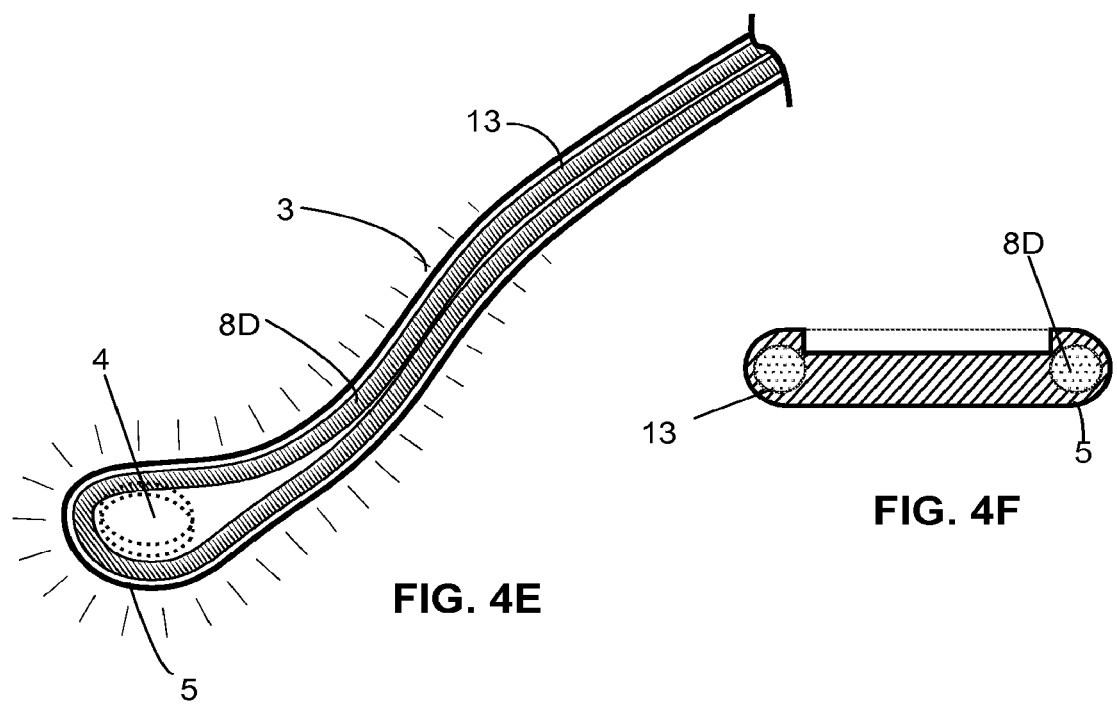
FIG. 4E is a schematic view of the wand of the luminescent ophthalmic-device of FIG. 1 depicting a wand including circulating chemiluminescent fluid, according to an embodiment.
FIG. 4F is a schematic, cross-sectional view of the chemiluminescent circulation line of the circulating chemiluminescent marker embodiment of FIG. 4C, according to an embodiment.

FIGS. 4E and 4F depict a second variant embodiment of a chemiluminescent marker 8 implemented as a pre-mixed, chemiluminescent liquid 8D circulating through channel 13 disposed throughout wand 3 and circumscribing a therapeutic material (not shown) disposed in cavity 4, according to an embodiment. It should be appreciated that chemiluminescent liquids also include non-luminescent liquid suspensions of chemiluminescent particulates and that circulation may be achieved through pumping, for example.

It should be appreciated that any combination of features set forth in particular embodiments are included within the scope of the present invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A luminescent ophthalmic device for placing a therapeutic agent into a treatment position, the device comprising:
   a light transmissive wand;
   a wand tip connected to the wand, the wand tip including a receptacle disposed within the wand tip, the receptacle configured to hold the therapeutic agent; and
   at least two luminescent markers disposed around the receptacle in the wand tip, the luminescent markers highlighting a boundary of the receptacle within the wand tip when viewed through transpupillary viewing methods; the luminescent markers activated by light propagated through the light transmissive wand.

2. The device of claim 1, wherein the light comprises visible light or ultra violet (UV) light.

3. The device of claim 1, wherein the wand tip is non-retractable.

4. The device of claim 1, wherein the at least two luminescent markers include a phosphorescent marker.

5. The device of claim 4, wherein the phosphorescent marker includes fluorescein or diphenyl oxalate.

6. The device of claim 1, wherein the light transmissive wand is implemented as a longitudinal, light-transmissive element configured to direct light propagation to the at least two luminescent markers.

7. The device of claim 6, wherein the longitudinal, light-transmissive element is implemented as the body of the wand itself.

8. The device of claim 1, wherein the at least two luminescent markers define a shape circumscribing the therapeutic agent when disposed in the receptacle.

9. The device of claim 1, wherein the two luminescent markers comprise a set of pegs integrally attached to an attachable wand tip.

10. The device of claim 6, wherein the longitudinal, light-transmissive element comprises a light pipe embedded in the body of the wand.

11. The device of claim 10, wherein the wand tip includes at least one embedded light emitting diode configured to direct light to the at least two luminescent markers.

12. The device of claim 11, wherein the at least two luminescent markers define a geometry circumscribing the therapeutic agent when disposed in the receptacle.

13. A device for placing a therapeutic agent into a treatment position, the device comprising:
   a light transmissive wand;
   a non-retractable wand tip connected to the wand, the wand tip including a cavity disposed within the wand tip, the cavity configured to hold a therapeutic agent; and
   at least two luminescent markers disposed around the cavity in the wand tip, the markers highlighting a boundary of the cavity within the wand tip when viewed through transpupillary viewing methods; the at least two luminescent markers activated by light propagated through the light transmissive wand, wherein the light transmissive wand is implemented as a longitudinal, light-transmissive element configured to direct light propagation to the at least two luminescent markers.

14. The device of claim 13, wherein the longitudinal, light-transmissive element is implemented as the body of the wand itself.

15. The device of claim 14, wherein the light comprises visible light or ultra violet (UV) light.

16. The device of claim 13, wherein the at least two luminescent markers include a phosphorescent marker.

17. The device of claim 16, wherein the phosphorescent marker includes fluorescein or diphenyl oxalate.

18. The device of claim 13, wherein the at least two luminescent markers define a shape circumscribing the therapeutic agent when disposed in the cavity.

19. The device of claim 13, wherein the longitudinal, light-transmissive element comprises a light pipe embedded in a body of the wand.

20. The device of claim 19, wherein the wand tip includes at least one embedded light emitting diode configured to direct light to the at least two luminescent markers.

* * * * *